(12) United States Patent
Okada et al.

(10) Patent No.: US 9,095,139 B2
(45) Date of Patent: Aug. 4, 2015

(54) HERBICIDAL COMPOSITION

(71) Applicant: SUMITOMO CHEMICAL COMPANY, LIMITED, Tokyo (JP)

(72) Inventors: Yukio Okada, Kawanishi (JP); Motofumi Mizutani, Kobe (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/152,277

(22) Filed: Jan. 10, 2014

(65) Prior Publication Data

US 2014/0128266 A1 May 8, 2014

Related U.S. Application Data

(63) Continuation of application No. 11/837,777, filed on Aug. 13, 2007, now abandoned.

(30) Foreign Application Priority Data

Aug. 16, 2006 (JP) ................................. 2006-221786

(51) Int. Cl.
*A01N 43/90* (2006.01)
*A01N 47/36* (2006.01)

(52) U.S. Cl.
CPC ............... *A01N 43/90* (2013.01); *A01N 47/36* (2013.01)

(58) Field of Classification Search
USPC ........................................................ 504/215
See application file for complete search history.

(56) References Cited

U.S. PATENT DOCUMENTS

2005/0032650 A1 * 2/2005 Tanaka et al. ................. 504/215

FOREIGN PATENT DOCUMENTS

| EP | 0124295 A2 | * | 11/1984 |
| EP | 1090551 A1 | | 4/2001 |
| JP | 5-43401 A | | 2/1993 |
| JP | 9-183704 A | | 7/1997 |
| JP | 9-278608 A | | 10/1997 |
| JP | 10-251107 A | | 9/1998 |
| JP | 11-349412 A | | 12/1999 |
| JP | 2005-126415 A | | 5/2005 |
| JP | 2005126415 A | * | 5/2005 |
| JP | 2005-239735 A | | 9/2005 |
| JP | 2005-325127 A | | 11/2005 |
| JP | 2006-257082 A | | 9/2006 |

OTHER PUBLICATIONS

Parenthetical expression. (2006). Grammatically Correct. Retrieved Sep. 27, 2010, from http://www.uhv.edu/ac/newsletters/writing/grammartip2006.08.29.htm.
Extended European Search Report issued Nov. 2007 in European Patent Application No. 07015403.4.
Summons to Attend Oral Proceedings issued Dec. 2, 2009 in European Patent Application No. 07015403.4.

* cited by examiner

*Primary Examiner* — Janet Epps-Smith
*Assistant Examiner* — Courtney Brown
(74) *Attorney, Agent, or Firm* — Sughrue Mion, PLLC

(57) ABSTRACT

In a herbicidal composition containing a sulfonylurea compound of the formula (I):

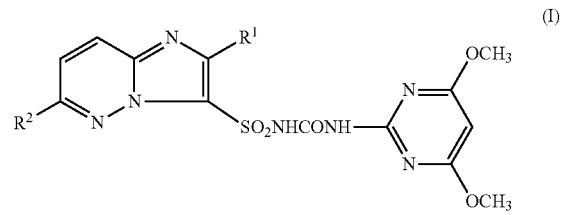

a carboxymethylcellulose salt, a ligninsulfonic acid salt, a surfactant and water, growth of particle of the sulfonylurea compound suspended in the herbicidal composition scarcely occurs after the storage.

11 Claims, No Drawings

HERBICIDAL COMPOSITION

CROSS REFERENCE TO RELATED APPLICATIONS

This application is a continuation of U.S. patent application Ser. No. 11/837,777, filed Aug. 13, 2007, which claims priority to Japanese Patent Application No. 2006-221786, filed Aug. 16, 2006, the contents of all of which are incorporated herein by reference.

TECHNICAL FIELD

The present invention directs to a herbicidal composition.

BACKGROUND ARTS

An aqueous suspended herbicidal composition is a formulation obtained by suspending a finely-ground solid poorly water-soluble herbicidal compound in water with a surfactant, dispersant and the like, and the solid poorly water-soluble herbicidal compound has a particle size of 5 μm or less, thus, the aqueous suspended herbicidal composition is expected to manifest a relatively high effect.

A sulfonylurea compound of the formula (I):

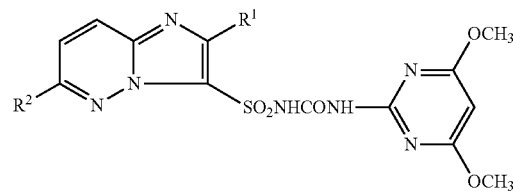

(wherein, $R^1$ represents a halogen atom and $R^2$ represents a $C_{2-4}$ alkyl group or cyclopropyl group.)
is known as a herbicidal active ingredient in USP2005-032650A. In USP2005-032650A, aqueous suspended herbicidal compositions containing the sulfonylurea compound are known in preparation examples 2 and 3.

Aqueous formulations containing the sulfonylurea compound of the formula (I) are generally unstable and particle size of the sulfonylurea compound of the formula (I) tend to increase in the aqueous formulation under preservation conditions. The present invention provides a stable formulation containing the sulfonylurea compound, in which the sulfonylurea compound scarcely shows growth of particle under preservation conditions.

DISCLOSURE OF THE INVENTION

The present invention provides the following herbicidal compositions, which are usually aqueous suspended compositions.

(Invention 1)
A herbicidal composition comprising a herbicidal sulfonylurea compound of the formula (I):

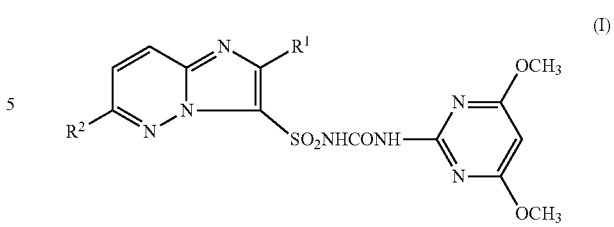

(wherein, $R^1$ represents a halogen atom and $R^2$ represents a $C_{2-4}$ alkyl group or cyclopropyl group.)
a carboxymethylcellulose salt,
a ligninsulfonic acid salt,
a surfactant and
water.

(Invention 2)
The herbicidal composition described in Invention 1, wherein the amount of the sulfonylurea compound of the formula (I) is 0.5 to 50 wt %, the amount of the carboxymethylcellulose salt is 0.01 to 5 wt %, the amount of the ligninsulfonic acid salt is 0.05 to 5 wt % and the amount of the surfactant is 0.1 to 10 wt %.

(Invention 3)
The herbicidal composition described in Invention 1 or 2, wherein $R^1$ represents a chlorine atom and $R^2$ represents a propyl group in the sulfonylurea compound of the formula (I).

(Invention 4)
The herbicidal composition described in any of Inventions 1 to 3, wherein the carboxymethylcellulose salt is a carboxymethylcellulose salt having a degree of etherification in the range of 0.4 to 1.0.

(Invention 5)
The herbicidal composition described in any of Inventions 1 to 4, wherein the ligninsulfonic acid salt is a ligninsulfonic acid salt having a degree of sulfonation of 2.5 or less.

(Invention 6)
The herbicidal composition described in any of Inventions 1 to 5, wherein the surfactant is a combination of at least one anionic surfactant and at least one nonionic surfactant.

The herbicidal composition of the present invention shows, under preservation conditions, scarce growth of particle of the sulfonylurea compound of the formula (I) suspended in the aqueous suspended herbicidal composition.

The herbicidal composition of the present invention is a composition containing a sulfonylurea compound of the formula (I), a carboxymethylcellulose salt, a ligninsulfonic acid salt, a surfactant and water, wherein the sulfonylurea compound is usually suspended in water.

The sulfonylurea compound can be produced by a method described, for example, in USP2005-032650A, and specifically mentioned are compounds described in Table 1.

TABLE 1

| Compound No. | $R^1$ | $R^2$ | Melting point (° C.) |
| --- | --- | --- | --- |
| 1 | Cl | $C_2H_5$ | 162-166 |
| 2 | Cl | $n\text{-}C_3H_7$ | 199-201 (decomposition) |
| 3 | Cl | $i\text{-}C_3H_7$ | 197-199 |
| 4 | Cl | $n\text{-}C_4H_9$ | 164-167 |
| 5 | Cl | $i\text{-}C_4H_9$ | 171-174 |
| 6 | Cl | $c\text{-}C_3H_5$ | 166-169 |
| 7 | F | $n\text{-}C_3H_7$ | 177.3-178.5 |

In the table, $C_2H_5$ represents an ethyl group, $n\text{-}C_3H_7$ represents a propyl group, $i\text{-}C_3H_7$ represents an isopropyl group, n-$C_4H_9$ represents a butyl group, i-$C_4H_9$ represents an isobutyl group, and c-$C_3H_5$ represents a cyclopropyl group.

The herbicidal composition of the present invention contain the sulfonylurea compound and optionally one or more other pesticidal compounds such as simetryn, dymron, propanil, mefenaset, phentolazamide, ethobenzanide, swep, oxadiclomefone, oxadiazolone, pyrazolate, prodiamine, cafenstrole, pentoxazone, clomeprop, pyriphthalide, benzobicyclon, bromobutide, pyraclonil, imazosulfuron and sulfosulfuron.

The herbicidal composition of the present invention usually contains the sulfonylurea compound of the formula (I) in an amount of 0.5 to 50 wt %, preferably 1 to 40 wt %. When the herbicidal composition contain the other pesticidal compound, the total amount of the pesticidal compounds is usually 0.5 to 50 wt %, preferably 1 to 40 wt %

The carboxymethylcellulose salt includes sodium salts, calcium salts and the like. In the present invention, those showing relatively low viscosity in being dissolved in water can be preferably used as the carboxymethylcellulose salt, and specifically, carboxymethylcellulose salts having a viscosity in 2 wt % aqueous solution of 1 to 100 mPa·s (type B viscometer, 60 rpm, 25° C.) are preferable. As such carboxymethylcellulose salts, carboxymethylcellulose salts having a degree of etherification in the range of 0.4 to 1.0 are mentioned.

As the carboxymethylcellulose salt to be used in the present invention, those commercially sold can be used, and examples thereof include CELLOGEN 6A (manufactured by Dai-ichi Kogyo Seiyaku Co., Ltd.), CELLOGEN 7A (manufactured by Dai-ichi Kogyo Seiyaku Co., Ltd.), CMC DAICEL 1110 (manufactured by Daicel Chemical Industry, Ltd.) and CMC DAICEL 1210 (manufactured by Daicel Chemical Industry, Ltd.).

In the herbicidal composition of the present invention, the carboxymethylcellulose salt is contained in an amount of usually 0.01 to 5 wt %, preferably 0.1 to 3 wt %.

The ligninsulfonic acid salt includes sodium salts, calcium salts, ammonium salts and the like. In the present invention, ligninsulfonic acid salts having a degree of sulfonation of 2.5 or less are preferably used.

As the ligninsulfonic acid salt to be used in the present invention, those commercially sold can be used, and examples thereof include NEWKALGEN WG-4 (manufactured by Takemoto Oil & Fat Co., Ltd.), NEWKALGEN RX-B (manufactured by Takemoto Oil & Fat Co., Ltd.), SAN X P201 (manufactured by Nippon Paper Chemicals Co., Ltd.), SAN X P-252 (manufactured by Nippon Paper Chemicals Co., Ltd.), VANILLEX N (manufactured by Nippon Paper Chemicals Co., Ltd.), PEARLLEX NP (manufactured by Nippon Paper Chemicals Co., Ltd.) and the like.

In the herbicidal composition of the present invention, the ligninsulfonic acid salt is contained in an amount of usually 0.05 to 5 wt %, preferably 0.1 to 3 wt %.

The surfactant to be contained in the herbicidal composition of the present invention contains at least one surfactant. In the present invention, examples of the surfactant which can be used include anionic surfactants such as polyoxyethylene arylphenyl ether phosphoric acid salts (e.g., NEWKALGEN FS-3EG, manufactured by Takemoto Oil & Fat Co., Ltd.), alkylsulfuric acid salts (e.g., MONOGEN Y-500: manufactured by Dai-ichi Kogyo Seiyaku Co., Ltd.), polyoxyethylene arylphenyl ether sulfuric acid salts (e.g., AGRISOL FL-2017: manufactured by Kao Corporation), polyoxyalkylene arylphenyl ether sulfuric acid salts (e.g., NEWKALGEN FS-7, manufactured by Takemoto Oil & Fat Co., Ltd.), dioctylsulfosuccinic acid salts (e.g., NEOCOL YSK: manufactured by Dai-ichi Kogyo Seiyaku Co., Ltd., SANMORIN OT-70: manufactured by Sanyo Chemical Industries, Ltd.) and the like; and nonionic surfactants such as sucrose fatty acid esters (e.g., NEWKALGEN FS-100, manufactured by Takemoto Oil & Fat Co., Ltd.), polyoxyethylene polyoxypropylene block polymers (e.g., NEWPOL PE68: manufactured by Sanyo Chemical Industries, Ltd.), polyoxyalkylene polyalkylene polyamine (e.g., NEWKALGEN D-3020, manufactured by Takemoto Oil & Fat Co., Ltd.), polyoxyethylene, alkylphenyl ether (e.g., NEWKALGEN D-410, manufactured by Takemoto Oil & Fat Co., Ltd.), polyoxyethylene aryl phenyl ether formaldehyde condensates (e.g., NEWKALGEN E-300, manufactured by Takemoto Oil & Fat Co., Ltd.), and the like.

In the present invention, the surfactant is preferably a combination of at least one anionic surfactant and at least one nonionic surfactant.

In the herbicidal composition of the present invention, the surfactant is contained in an amount of usually 0.1 to 10 wt %.

The herbicidal composition of the present invention is a composition obtained by dispersing or dissolving the sulfonylurea compound of the formula (I), a carboxymethylcellulose salt, a ligninsulfonic acid salt, a surfactant and optionally the other pesticidal compound, auxiliaries for pesticidal formulation in water. The water can be tap water, well water, ion-exchanged water and the like. In the present invention, the amount of water is usually 30 to 90 wt %, preferably 50 to 80 wt %.

The herbicidal composition of the present invention may contain, if necessary, auxiliaries for pesticidal formulation in addition to the above-mentioned components. Examples of the auxiliaris for pesticidal formulation include suspension-assistant agents, antifreezing agents, pH regulating agents, antifoaming agents, preservatives and the like. These auxiliaries for pesticidal formulation can be selected appropriately depending on the kind of the surfactant and the like to be used and the content of the sulfonylurea compound.

Examples of the suspension-assistant agent include montmorillonite type mineral fine powders, anhydrous silica fine powders and the like. When a montmorillonite type mineral fine powder is used as the suspension-assistant agent in the herbicidal composition of the present invention, dispersibility of solid phase is excellent in dilution of the aqueous suspended herbicidal composition in water. As the montmorillonite type mineral fine powder, those generally sold commercially as bentonite or high purity montmorillonite can be used. When the suspension-assistant agent is used, its amount is usually 0.1 to 3 wt % based on the aqueous suspended herbicidal composition of the present invention.

Examples of the antifreezing agent include ethylene glycol, diethylene glycol, glycerin and propylene glycol. When the antifreezing agent is used, its amount is usually 1 to 20 wt %, preferably 3 to 12 wt %.

Examples of the pH regulating agent include citric acid monohydrate, sorbic acid and potassium sorbate.

As the antifoaming agent, for example, silicone-based antifoaming agents and the like are used. When the pH regulating agent is used, its amount is usually 0.01 to 5 wt %, preferably 0.5 to 3 wt %. When the antifoaming agent is used, its amount is usually 0.05 to 0.5 wt %, preferably 0.05 to 0.3 wt %.

As the preservative, for example, butylparaben (butyl p-hydroxybenzoate), sorbic acid, potassium sorbate are used. When the preservative is used, its amount is usually 0.01 to 3 wt %, preferably 0.01 to 1.5 wt %.

As the herbicidal composition of the present invention, the following embodiments are exemplified.

An aqueous suspended herbicidal composition containing 0.5 to 50 wt % of the sulfonylurea compound, 0.01 to 5 wt % of a carboxymethylcellulose salt, 0.05 to 5 wt % of a ligninsulfonic acid salt, 0.1 to 10 wt % of a surfactant, and water.

An aqueous suspended herbicidal composition containing 0.5 to 50 wt % of the sulfonylurea compound, 0.01 to 5 wt % of a carboxymethylcellulose salt having a degree of etherification of 0.6 to 1.0, 0.05 to 5 wt % of a ligninsulfonic acid salt having a degree of sulfonation of 2.5 or less, 0.1 to 10 wt % of a surfactant, and water.

An aqueous suspended herbicidal composition containing 0.5 to 50 wt % of the sulfonylurea compound, 0.01 to 5 wt % of a carboxymethylcellulose salt having a degree of etherification of 0.6 to 1.0, 0.05 to 5 wt % of a ligninsulfonic acid salt having a degree of sulfonation of 2.5 or less, 0.1 to 10 wt % of surfactants composed of at least one anionic surfactant and at least one nonionic surfactant, and water.

An aqueous suspended herbicidal composition containing 0.5 to 50 wt % of the sulfonylurea compound, 0.01 to 5 wt % of a carboxymethylcellulose salt, 0.05 to 5 wt % of a ligninsulfonic acid salt, 0.1 to 10 wt % of a surfactant, and 50 to 80 wt % of water.

An aqueous suspended herbicidal composition containing 0.5 to 50 wt % of the sulfonylurea compound, 0.01 to 5 wt % of a carboxymethylcellulose salt having a degree of etherification of 0.6 to 1.0, 0.05 to 5 wt % of a ligninsulfonic acid salt having a degree of sulfonation of 2.5 or less, 0.1 to 10 wt % of a surfactant, and 50 to 80 wt % of water.

An aqueous suspended herbicidal composition containing 0.5 to 50 wt % of the sulfonylurea compound, 0.01 to 5 wt % of a carboxymethylcellulose salt having a degree of etherification of 0.6 to 1.0, 0.05 to 5 wt % of a ligninsulfonic acid salt having a degree of sulfonation of 2.5 or less, 0.1 to 10 wt % of surfactants composed of at least one anionic surfactant and at least one nonionic surfactant, and 50 to 80 wt % of water.

An aqueous suspended herbicidal composition consisting essentially of 0.5 to 50 wt % of the sulfonylurea compound and another pesticidal compound, 0.01 to 5 wt % of a carboxymethylcellulose salt, 0.05 to 5 wt % of a ligninsulfonic acid salt, 0.1 to 10 wt % of a surfactant, an auxiliary for pesticidal formulation, and water.

An aqueous suspended herbicidal composition consisting essentially of 0.5 to 50 wt % of the sulfonylurea compound and another pesticidal compound, 0.01 to 5 wt % of a carboxymethylcellulose salt having a degree of etherification of 0.6 to 1.0, 0.05 to 5 wt % of a ligninsulfonic acid salt having a degree of sulfonation of 2.5 or less, 0.1 to 10 wt % of a surfactant, an auxiliary for pesticidal formulation, and water.

An aqueous suspended herbicidal composition consisting essentially of 0.5 to 50 wt % of the sulfonylurea compound and another pesticidal compound, 0.01 to 5 wt % of a carboxymethylcellulose salt having a degree of etherification of 0.6 to 1.0, 0.05 to 5 wt % of a ligninsulfonic acid salt having a degree of sulfonation of 2.5 or less, 0.1 to 10 wt % of surfactants composed of at least one anionic surfactant and at least one nonionic surfactant, an auxiliary for pesticidal formulation, and water.

The herbicidal composition of the present invention can be produced, for example, by a method described below.

A method (production method 1) in which the sulfonylurea compound, a carboxymethylcellulose salt, a ligninsulfonic acid salt, a surfactant and, an auxiliary for pesticidal formulation if necessary, are added to water, and the mixture is sufficiently stirred and mixed, for example, by a high speed stirrer, then, finely-ground and dispersed, for example, by a wet-pulverizer such as dinomill and micro-fluidizer, and a method (production method 2) in which an original powder of the sulfonylurea compound is finely-ground by a dry-pulverizer such as jetmizer, then, this is added together with other components to water, and the mixture is stirred and mixed for about 30 to 90 minutes to cause dispersion thereof by a high speed stirrer.

The pesticidal component in the aqueous suspended herbicidal composition of the present invention is dispersed in the form of fine particle in water, and the average particle size of the fine particles is 10 μm or less, preferably 0.2 to 5 μm.

The herbicidal composition of the present invention can be used by spraying itself or, if desired, by dilution with water before applying, according to known methods, and for example, the composition can also be sprayed directly from levee into paddy field under flood irrigation. When the herbicidal composition of the present invention is sprayed itself into paddy field and the like, a vessel containing the herbicidal composition of the present invention is shaken slightly before use, then, the composition is sprayed in portions along levee. When the herbicidal composition of the present invention is diluted with water before applying, the composition is sprayed on the surface of soil, sprayed on stem and leaves, and the like using known spraying devices in paddy field, dry field, orchard, turf, non-cultivated field and the like. Also, the water-diluted liquid can be used in a seed treatment, nursery box treatment and the like.

EXAMPLES

The present invention will be illustrated further in detail by the following examples, but the present invention is not limited to these examples.

Production Example 1

To 1.8 parts by weight of the compound No. 2, 0.1 part by weight of sorbic acid, 0.3 parts by weight of a silicone-based antifoaming agent (Antifoam E-20, manufactured by Kao Corporation), 0.5 parts by weight of a sucrose fatty acid ester (NEWKALGEN FS-100, manufactured by Takemoto Oil & Fat Co., Ltd.), 0.8 parts by weight of a polyoxyethylene arylphenyl ether phosphoric acid salt (NEWKALGEN FS-3EG, manufactured by Takemoto Oil & Fat Co., Ltd.), 0.2 parts by weight of sodium laurylsulfate (MONOGEN Y-500: manufactured by Dai-ichi Kogyo Seiyaku Co., Ltd.) and 1.0 part by weight of sodium montmorillonite (KUNIPIA F, manufactured by Kuminine Industries Co., Ltd.) were added 30.3 parts by weight of ion-exchanged water, and they were mixed and dispersed, then, wet-pulverized using Dinomill KDL (manufactured by Shinmaru Enterprises Corporation) to obtain a suspension (1) of the compound No. 2.

On the other hand, 2.0 parts by weight of sodium carboxymethylcellulose (CELLOGEN 7A, Degree of etherification: 0.7~0.8, manufactured by Dai-ichi Kogyo Seiyaku Co., Ltd.) and 0.1 part by weight of sodium ligninsulfonate (VANILLEX N, Degree of sulfonation: 0.13, manufactured by Nippon Paper Chemicals Co., Ltd.) were added to 50.9 parts by weight of ion-exchanged water to cause dissolution thereof, obtaining an aqueous solution (1).

To 35 parts by weight of a suspension (1) of the compound No. 2 was added 53 parts by weight of an aqueous solution (1) and 12 parts by weight of propylene glycol to give a total amount of 100 parts by weight, and they were stirred and mixed to obtain an aqueous suspended herbicidal composition (1) having a content of the compound No. 2 of 1.8 wt %.

Comparative Production Example 1

2.0 parts by weight of sodium carboxymethylcellulose (CELLOGEN 7A, Degree of etherification: 0.7~0.8, manufactured by Dai-ichi Kogyo Seiyaku Co., Ltd.) was added to 53 parts by weight of ion-exchanged water to cause dissolution thereof, obtaining an aqueous solution (a).

To 35 parts by weight of the suspension (1) of the compound No. 2 in Production Example 1, 53 parts by weight of the aqueous solution (a) and 12 parts by weight of propylene glycol were added to give a total amount of 100 parts by weight, and they were stirred and mixed, to obtain an aqueous suspended herbicidal composition (a) having a content of the compound No. 2 of 1.8 wt %.

Test Example 1

Particle Size Measurement

The volume median diameter was measured of the aqueous suspended herbicidal compositions (1) and (a) using a laser diffraction type particle size distribution measurement apparatus (HEROS & RODOS, manufactured by Japan Laser Corp., measurement conditions: focus length 20 mm, dispersing medium is ion-exchanged water).

The results are shown in Table 2.

TABLE 2

| Herbicidal composition | (1) | (a) |
|---|---|---|
| directly after production | 1.7 μm | 1.7 μm |
| 7 days after storage at room temperature | 1.7 μm | 8.3 μm |
| 7 days after storage at 40° C. | 1.6 μm | 13.6 μm |
| 7 days after storage at 60° C. | 1.6 μm | 17.4 μm |

Production Example 2

To 10.5 parts by weight of the compound No. 2, 0.1 part by weight of sorbic acid, 0.2 parts by weight of a silicone-based antifoaming agent (Antifoam E-20, manufactured by Kao Corporation), 10.0 parts by weight of ethylene glycol, 3.0 parts by weight of a sucrose fatty acid ester (e.g., NEWKALGEN FS-100, manufactured by Takemoto Oil & Fat Co., Ltd.), 6.0 parts by weight of a polyoxyethylenearyl phenyl ether sulfuric acid salt (AGRISOL FL-2017, manufactured by Kao Corporation), 1.0 part by weight of sodium ligninsulfonate (VANILLEX N, Degree of sulfonation: 0.13, manufactured by Nippon Paper Chemicals Co., LTd.), 2.0 parts by weight of AEROSIL COK84 (high purity anhydrous silica, manufactured by Japan AEROSIL Co., Ltd.) and 2.0 parts by weight of sodium carboxymethylcellulose (CELLOGEN 7A, Degree of etherification: 0.7~0.8, manufactured by Dai-ichi Kogyo Seiyaku Co., Ltd.), 65.2 parts by weight of ion-exchanged water were added, and they were mixed and dispersed, then, wet-pulverized using Dinomill KDL (manufactured by Shinmaru Enterprises Corporation) to obtain an aqueous suspended herbicidal composition (2) having a content of the compound No. 2 of 10.5 wt %.

Production Example 3

To 1.8 parts by weight of the compound No. 2, 16.9 parts by weight of bromobutide, 0.1 part by weight of sorbic acid, 0.3 parts by weight of a silicone-based antifoaming agent (Antifoam E-20, manufactured by Kao Corporation), 7.6 parts by weight of ethylene glycol, 2.0 parts by weight of a sucrose fatty acid ester (NEWKALGEN FS-100, manufactured by Takemoto Oil & Fat Co., Ltd.), 0.8 parts by weight of a polyoxyethylenearyl phenyl ether phosphoric acid salt (NEWKALGEN FS-3EG, manufactured by Takemoto Oil & Fat Co., Ltd.), 0.2 parts by weight of sodium ligninsulfonate (VANILEX N, Degree of sulfonation: 0.13, manufactured by Nippon Paper Chemicals Co., LTd.) and 0.8 part by weight of sodium montmorillonite (KUNIPIA F, manufactured by Kuminine Industries Co., Ltd.), 49.5 parts by weight of ion-exchanged water were added, and they were mixed and dispersed, then, wet-pulverized using Dinomill KDL (manufactured by Shinmaru Enterprises Corporation) to obtain a suspension (3) of the compound No. 2 and bromobutide.

On the other hand, 0.4 parts by weight of carboxymethylcellulose sodium (CELLOGEN 7A, Degree of etherification: 0.7~0.8, manufactured by Dai-ichi Kogyo Seiyaku Co., Ltd.) and 0.2 part by weight of sodium laurylsulfate (MONOGEN Y-500, manufactured by Dai-ichi Kogyo Seiyaku Co., Ltd.) were added to 19.4 parts by weight of ion-exchanged water to cause dissolution thereof, obtaining an aqueous solution (3).

To 80 parts by weight of a suspension (3) of the compound No. 2, 20 parts by weight of the aqueous solution (3) was added to give a total amount of 100 parts by weight, and they were stirred and mixed to obtain an aqueous suspended herbicidal composition (3) having a content of the compound No. 2 of 1.8 wt % and a content of bromobutide of 16.9 wt %.

Test Example 2

Particle Size Measurement

The volume median diameter was measured of the aqueous suspended herbicidal compositions (2) and (3) using a laser diffraction type particle size distribution measurement apparatus (HEROS & RODOS, manufactured by Japan Laser Corp., measurement conditions: focus length 20 mm, dispersing medium is ion-exchanged water).

The results are shown in Table 3.

TABLE 3

| Herbicide composition | (2) | (3) |
|---|---|---|
| directly after production | 2.5 μm | 1.9 μm |
| 20 days after storage at room temperature | 2.4 μm | un-measured |
| 30 days after storage at room temperature | un-measured | 1.9 μm |
| 14 days after storage at 40° C. | 2.3 μm | un-measured |
| 30 days after storage at 40° C. | un-measured | 1.8 μm |
| 14 days after storage at −18° C. | 2.4 μm | 1.8 μm |

Production Example 4

To 1.8 parts by weight of the compound No. 2, 0.1 part by weight of sorbic acid, 0.3 parts by weight of a silicone-based antifoaming agent (Antifoam E-20, manufactured by Kao Corporation), 7.6 parts by weight of propylene glycol, 0.5 parts by weight of a sucrose fatty acid ester (NEWKALGEN FS-100, manufactured by Takemoto Oil & Fat Co., Ltd.), 0.8 parts by weight of a polyoxyethylenearyl phenyl ether phosphoric acid salt (NEWKALGEN FS-3PG, manufactured by Takemoto Oil & Fat Co., Ltd.), 0.1 part by weight of sodium ligninsulfonate (NEWKALGEN WG-4, Degree of sulfonation: 1.7, manufactured by Takemoto Oil & Fat Co., Ltd.), 0.2 parts by weight of sodium lauryl sulfate (MONOGEN Y-500, manufactured by Dai-ichi Kogyo Seiyaku Co., Ltd.) and 0.8 part by weight of sodium montmorillonite (KUNIPIA F, manufactured by Kuminine Industries Co., Ltd.), 22.8 parts by weight of ion-exchanged water were added, and they were mixed and dispersed, then, wet-pulverized using Dinomill KDL (manufactured by Shinmaru Enterprises Corporation) to obtain a suspension (4) of the compound No. 2.

On the other hand, 2.0 parts by weight of carboxymethylcellulose sodium (CELLOGEN 7A, Degree of etherification: 0.7~0.8, manufactured by Dai-ichi Kogyo Seiyaku Co., Ltd.) were added to 63.0 parts by weight of ion-exchanged water to cause dissolution thereof, obtaining an aqueous solution (4).

To 35 parts by weight of a suspension (4) of the compound No. 2, 65 parts by weight of the aqueous solution (4) were added to give a total amount of 100 parts by weight, and they were stirred and mixed to obtain an aqueous suspended herbicidal composition (4) having a content of the compound No. 2 of 1.8 wt %.

Comparative Production Example 2

To 35 parts by weight of a suspension (4) of the compound No. 2, 65 parts by weight of ion-exchanged water were added to give a total amount of 100 parts by weight, and they were stirred and mixed to obtain an aqueous suspended herbicidal composition (b) having a content of the compound No. 2 of 1.8 wt %.

Test Example 3

Particle Size Measurement

The volume median diameter was measured of the aqueous suspended herbicidal compositions (4) and (b) using a laser diffraction type particle size distribution measurement apparatus (HEROS & RODOS, manufactured by Japan Laser Corp., measurement conditions: focus length 20 mm, dispersing medium is ion-exchanged water).

The results are shown in Table 4.

TABLE 4

| Herbicide composition | (4) | (b) |
|---|---|---|
| directly after production | 2.0 μm | 1.8 μm |
| 30 days after storage at room temperature | 1.9 μm | 1.7 μm |
| 30 days after storage at 40° C. | 1.8 μm | 1.7 μm |
| 30 days after storage at 60° C. | 1.7 μm | 15.5 μm |

INDUSTRIAL APPLICABILITY

According to the herbicidale composition of the present invention, growth of particle of a sulfonylurea compound of the formula (I) suspended in the herbicidal composition scarcely occurs after the storage.

The invention claimed is:

1. A herbicidal composition comprising a sulfonylurea compound of the formula (I):

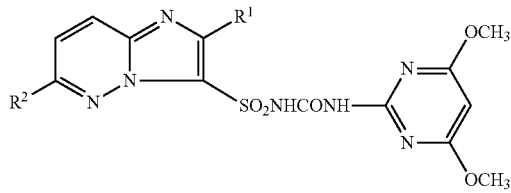

wherein, $R^1$ represents a halogen atom and $R^2$ represents a $C_{2-4}$ alkyl group or cyclopropyl group;
sodium carboxymethylcellulose;
a ligninsulfonic acid salt;
a surfactant; and
water excluding aqueous suspended herbicidal compositions containing an effective amount of pyraclonil.

2. The herbicidal composition according to claim 1, wherein the amount of the sulfonylurea herbicidal active compound of the formula (I) is 0.5 to 50 wt %, the amount of the sodium carboxymethylcellulose is 0.01 to 5 wt %, the amount of the ligninsulfonic acid salt is 0.05 to 5 wt % and the amount of the surfactant is 0.1 to 10 wt %, based on the aqueous suspended herbicidal composition.

3. The herbicidal composition according to claim 1 or 2 wherein, $R^1$ represents a chlorine atom and $R^2$ represents a propyl group in the sulfonylurea herbicidal active compound of the formula (I).

4. The herbicidal composition according to claim 1 or 2, wherein the sodium carboxymethylcellulose has a degree of etherification in the range of 0.4 to 1.0.

5. The herbicidal composition according to claim 1 or 2, wherein the ligninsulfonic acid salt is a ligninsulfonic acid salt having a degree of sulfonation of 2.5 or less.

6. The herbicidal composition according to claim 1 or 2, wherein the surfactant is a combination of at least one anionic surfactant and at least one nonionic surfactant.

7. The herbicidal composition according to claim 1 or 2, wherein the ligninsulfonic acid salt is selected from the group consisting of sodium salts, calcium salts, and ammonium salts.

8. The herbicidal composition according to claim 1 or 2, wherein the ligninsulfonic acid salt is a sodium salt.

9. The herbicidal composition according to claim 3, wherein the sodium carboxymethylcellulose has a degree of etherification in the range of 0.4 to 1.0, and the ligninsulfonic acid salt is a ligninsulfonic acid salt having a degree of sulfonation of 2.5 or less.

10. The herbicidal composition according to claim 3, wherein the ligninsulfonic acid salt is a sodium ligninsulfonate.

11. The herbicidal composition according to claim 9, wherein the ligninsulfonic acid salt is a sodium ligninsulfonate.

* * * * *